US012636635B2

(12) United States Patent
Tucker et al.

(10) Patent No.: US 12,636,635 B2
(45) Date of Patent: May 26, 2026

(54) ELASTOMERIC LAMINATE

(71) Applicant: Kimberly-Clark Worldwide, Inc., Neenah, WI (US)

(72) Inventors: John D. Tucker, Canton, GA (US); Glynis A. Walton, Roswell, GA (US); Shawn E. Jenkins, Suwanee, GA (US); Patricia H. Calhoun, Alpharetta, GA (US); Jeffrey Krueger, Roswell, GA (US); Wade R. Thompson, Cumming, GA (US); Fang Wang, Alpharetta, GA (US); Mehdi Gholipour, Roswell, GA (US); Simon Poruthoor, Alpharetta, GA (US); Ray Sterling, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 824 days.

(21) Appl. No.: 17/908,334

(22) PCT Filed: Mar. 31, 2021

(86) PCT No.: PCT/US2021/025211
§ 371 (c)(1),
(2) Date: Aug. 31, 2022

(87) PCT Pub. No.: WO2021/202761
PCT Pub. Date: Oct. 7, 2021

(65) Prior Publication Data
US 2023/0089861 A1    Mar. 23, 2023

Related U.S. Application Data

(60) Provisional application No. 63/132,387, filed on Dec. 30, 2020, provisional application No. 63/003,427, filed on Apr. 1, 2020.

(51) Int. Cl.
*B01J 20/26* (2006.01)
*A61L 15/22* (2006.01)
(Continued)

(52) U.S. Cl.
CPC ........... *B01J 20/261* (2013.01); *A61L 15/225* (2013.01); *A61L 15/42* (2013.01); (Continued)

(58) Field of Classification Search
CPC ...... A61L 15/225; A61L 15/42; B01J 20/261; B01J 20/28023; B01J 20/28035; D01F 8/00; D01F 8/04; D01F 8/06
See application file for complete search history.

(56) References Cited

U.S. PATENT DOCUMENTS

2014/0066873 A1* 3/2014 Kawakami ................ D01F 8/06
442/353
2015/0299918 A1* 10/2015 Kumihiro ................. D01F 8/06
442/329

FOREIGN PATENT DOCUMENTS

CN          1246164 A        3/2000
CN          1270552 A       10/2000
(Continued)

OTHER PUBLICATIONS

JP 2012-087450 Machine Translation (Year: 2012).*
(Continued)

*Primary Examiner* — Zachary M Davis
(74) *Attorney, Agent, or Firm* — Dority & Manning, P.A.

(57) ABSTRACT

Methods and (articles of manufacture therefrom) including forming an elastic film from a polymer composition; tensioning the elastic film to a stretch ratio of between 2 and 6 in the MD; laminating the elastic film to an extensible facing to provide an elastomeric laminate having a CD hysteresis loss of 70% or less and an MD hysteresis loss of 50% or less.

21 Claims, 4 Drawing Sheets

(51) Int. Cl.

| | |
|---|---|
| *A61L 15/42* | (2006.01) |
| *B01J 20/28* | (2006.01) |
| *B32B 5/02* | (2006.01) |
| *B32B 5/04* | (2006.01) |
| *B32B 5/08* | (2006.01) |
| *B32B 7/12* | (2006.01) |
| *B32B 37/15* | (2006.01) |
| *C08F 110/02* | (2006.01) |
| *C08L 23/16* | (2006.01) |
| *D01F 1/04* | (2006.01) |
| *D01F 1/10* | (2006.01) |
| *D01F 8/06* | (2006.01) |
| *D04H 3/007* | (2012.01) |
| *D04H 3/147* | (2012.01) |
| *D04H 3/16* | (2006.01) |

(52) U.S. Cl.

CPC ... *B01J 20/28023* (2013.01); *B01J 20/28035* (2013.01); *B01J 20/28038* (2013.01); *B32B 5/022* (2013.01); *B32B 5/04* (2013.01); *B32B 5/08* (2013.01); *B32B 7/12* (2013.01); *B32B 37/15* (2013.01); *C08F 110/02* (2013.01); *C08L 23/16* (2013.01); *D01F 1/04* (2013.01); *D01F 1/10* (2013.01); *D01F 8/06* (2013.01); *D04H 3/007* (2013.01); *D04H 3/147* (2013.01); *D04H 3/16* (2013.01); *B32B 2262/0207* (2013.01); *B32B 2262/0253* (2013.01); *B32B 2262/124* (2021.05); *B32B 2307/302* (2013.01); *B32B 2307/51* (2013.01); *B32B 2307/518* (2013.01); *B32B 2307/54* (2013.01); *B32B 2307/726* (2013.01); *D10B 2321/021* (2013.01); *D10B 2321/022* (2013.01); *D10B 2401/061* (2013.01); *D10B 2401/063* (2013.01); *D10B 2509/00* (2013.01); *D10B 2509/02* (2013.01)

(56) References Cited

FOREIGN PATENT DOCUMENTS

| | | | | |
|---|---|---|---|---|
| CN | 101903455 A | 12/2010 | | |
| CN | 101951863 A | 1/2011 | | |
| CN | 102689482 A | 9/2012 | | |
| CN | 104769172 A | 7/2015 | | |
| CN | 106414073 A | 2/2017 | | |
| CN | 110461936 A | 11/2019 | | |
| EP | 948556 A1 * | 10/1999 | ........... | A61F 13/514 |
| EP | 0948556 | 3/2002 | | |
| EP | 1519832 | 10/2010 | | |
| JP | 2010115869 A | 5/2010 | | |
| JP | 2012087450 A * | 5/2012 | .............. | D01D 5/34 |

OTHER PUBLICATIONS

Chinese Search Report Corresponding to Application No. 202180032443.7 on Apr. 12, 2024.

International Search Report and Written Opinion for PCT/US2021/025211 dated Jul. 21, 2021.

Chinese Search Report Corresponding to Application No. 202180032443.7 on Feb. 26, 2025.

\* cited by examiner

ELASTOMERIC LAMINATE

RELATED APPLICATIONS

The present application is the National Stage entry of International Patent Application No. PCT/US2021/025211 filed on Mar. 31, 2021, which is based on and claims priority to U.S. Provisional Patent application Ser. No. 63/003,427, filed on Apr. 1, 2020, and U.S. Provisional Patent application Ser. No. 63/132,387, filed on Dec. 30, 2020, which are incorporated herein by reference.

BACKGROUND

The present invention generally relates to elastomeric laminate materials.

Elastic composites are often used in products such as diapers and training pants to improve their ability to better fit the contours of the body. For example, an elastic composite may be formed from an elastic film and one or more nonwoven web materials. The nonwoven web material may be joined to the elastic film while the film is in a stretched condition so that the nonwoven web material can gather between the locations where it is bonded to the film when it is relaxed. The resulting elastic composite is stretchable in one direction (sometimes referred to as the machine direction) to the extent that the nonwoven web material gathered between the bond locations allows the elastic film to elongate. However, a wearer's movements often result in tensioning of the composite in multiple directions where such conventional elastic composites have limited stretch and retraction.

SUMMARY

In general, the subject matter of this specification relates to elastomeric composites or laminates. One aspect of the subject matter described in this specification can be implemented in a method that includes forming an elastic film from a polymer composition; tensioning the elastic film to a stretch ratio of between 2 and 6 in the MD; laminating the elastic film to an extensible facing, to provide an elastomeric laminate having a CD hysteresis loss of 70% or less and an MD hysteresis loss of 50% or less. Other embodiments of this aspect include corresponding products.

Particular embodiments of the subject matter described in this specification can be implemented so as to realize one or more of the following advantages. For example, by using the extensible facing as described herein, an elastic laminate can have enhanced stretch (and, in some implementations, retraction) properties such that it stretches in both the cross and machine directions to increase its drapeability and feel more like a fabric. This type of dual axis stretch is often called omni- or bi-axial stretch. Given these types of laminates can be used for human body contacting applications, like diapers, such biaxial stretch results in a more comfortable wearing experience for the wearer including being less constricted in her movements.

In some implementations, in addition to the biaxial stretch capabilities, the laminate also has biaxial retraction capabilities such that when it is stretched, the laminate retracts and (materially) recovers its initial shape/properties more effectively than conventional elastic laminates. This results in a snug fitting, yet comfortable, wearing experience that with time retains its "snugness" better. For example, if a diaper lost its snugness it would be more prone to leak and be less comfortable to wear.

The details of one or more implementations of the subject matter described in this specification are set forth in the accompanying drawings and the description below. Other features, aspects, and advantages of the subject matter will become apparent from the description, the drawings, and the claims.

DESCRIPTION OF DRAWINGS

Like reference symbols in the various drawings indicate like elements.

DETAILED DESCRIPTION

Figure 1A:
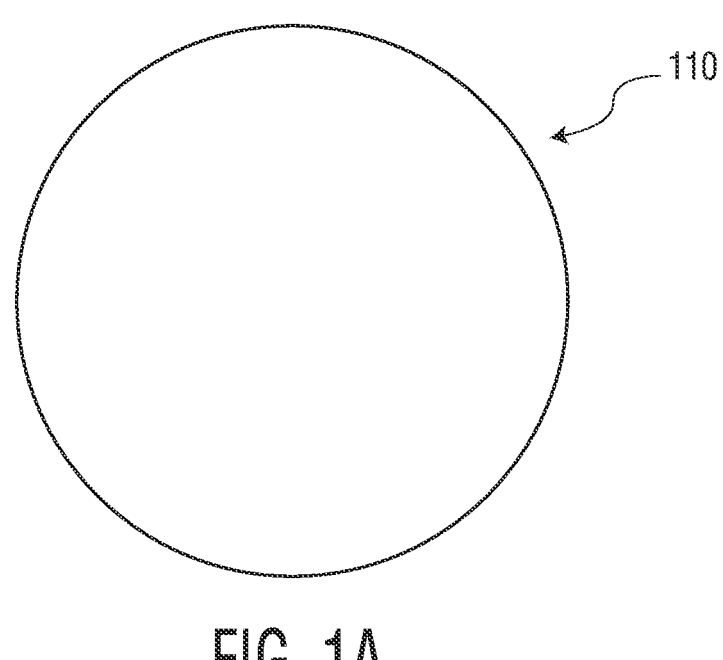
FIGS. 1A and 1B are example fibers for use in an extensible facing.

The present disclosure generally relates to an elastomeric laminate having a stretched elastic film bonded to a relaxed extensible or elastomeric facing to enable improved biaxial stretch and recovery properties, i.e., stretch and recovery in both the machine direction (MD) and cross machine direction or cross-machine direction (CD). Such elastomeric laminates can be used in, for example, personal care products including diapers, training pants and other absorbent articles.

As used herein, the terms "about," "approximately," or "generally," when used to modify a value, indicates that the value can be raised or lowered by 10%, such as, such as 7.5%, 5%, such as 4%, such as 3%, such as 2%, such as 1%, and remain within the disclosed aspect. Moreover, the term "substantially free of" when used to describe the amount of substance in a material is not to be limited to entirely or completely free of and may correspond to a lack of any appreciable or detectable amount of the recited substance in the material. Thus, e.g., a material is "substantially free of" a substance when the amount of the substance in the material is less than the precision of an industry-accepted instrument or test for measuring the amount of the substance in the material. In certain example embodiments, a material may be "substantially free of" a substance when the amount of the substance in the material is less than 10%, less than 9%, less than 8%, less than 7%, less than 6%, less than 5%, less than 4%, less than 3%, less than 2%, less than 1%, less than 0.5%, or less than 0.1% by weight of the material As used herein, the term "elastomeric" and "elastic" and refers to a material that, upon application of a stretching force, is stretchable in at least one direction (such as the CD or MD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein, the term "fibers" generally refer to elongated extrudates that may be formed by passing a polymer through a forming orifice, such as a die. Unless noted otherwise, the term "fibers" includes discontinuous fibers having a definite length (e.g., stable fibers) and substantially continuous filaments. Substantially continuous filaments may, for instance, have a length much greater than their diameter, such as a length to diameter ratio ("aspect ratio") greater than about 15,000 to 1, and in some cases, greater than about 50,000 to 1.

As used herein the term "extensible" generally refers to a material that stretches or extends in the direction of an applied force (e.g., CD or MD direction) by about 50% or more, in some aspects about 75% or more, in some aspects about 100% or more, and in some aspects, about 200% or more of its relaxed length or width.

As used herein, the terms "necked" and "necked material" generally refer to any material that has been drawn in at least one dimension (e.g., machine direction) to reduce its transverse dimension (e.g., cross machine direction) so that when the drawing force is removed, the material may be pulled back to its original width. The necked material generally has a higher basis weight per unit area than the un-necked material. When the necked material is pulled back to its original width, it should have about the same basis weight as the un-necked material. This differs from the orientation of a film in which the film is thinned and the basis weight is reduced. The necking method typically involves unwinding a material from a supply roll and passing it through a brake nip roll assembly driven at a given linear speed. A take-up roll or nip, operating at a linear speed higher than the brake nip roll, draws the material and generates the tension needed to elongate and neck the material.

As used herein the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No.

3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the terms "machine direction" or "MD" generally refers to the direction in which a material is produced (e.g., the direction the material is conveyed during the forming/manufacturing process of the nonwoven material). The term "cross-machine direction" or "CD" refers to the direction perpendicular to the machine direction.

As used herein, the term "thermal point bonding" generally refers to a process performed, for example, by passing a material between a patterned roll (e.g., calender roll) and another roll (e.g., anvil roll), which may or may not be patterned. One or both of the rolls are typically heated.

As used herein, the term "ultrasonic bonding" generally refers to a process performed, for example, by passing a material between a sonic horn and a patterned roll (e.g., anvil roll). For instance, ultrasonic bonding through the use of a stationary horn and a rotating patterned anvil roll is described in U.S. Pat. No. 3,939,033 to Grgach, et al., U.S. Pat. No. 3,844,869 to Rust Jr., and U.S. Pat. No. 4,259,399 to Hill, which are incorporated herein in their entirety by reference thereto for all purposes. Moreover, ultrasonic bonding through the use of a rotary horn with a rotating patterned anvil roll is described in U.S. Pat. No. 5,096,532 to Neuwirth, et al., U.S. Pat. No. 5,110,403 to Ehlert, and U.S. Pat. No. 5,817,199 to Brennecke, et al., which are incorporated herein in their entirety by reference thereto for all purposes. Of course, any other ultrasonic bonding technique may also be used in the present disclosure.

Generally speaking, this description is directed to a nonwoven composite (or referred to as a laminate) that contains an elastic film (e.g., film 10) laminated to one or more nonwoven web materials (e.g., an extensible or elastomeric facing 30). The composite is formed by passing the film through a nip to bond the film to the nonwoven web material(s). In some implementations, concurrent with bonding, apertures are also formed in the elastic film. The apertures are of a size sufficient to provide a desired level of texture, softness, hand feel, and/or aesthetic appeal to the composite without having a significant adverse effect on its elastic properties. Aperture and bond formation are accomplished, for example, by selectively controlling certain parameters of the lamination process, such as film content, bonding pattern, degree of film tension, bonding conditions, etc. In other implementations, the film is not apertured. Elastomeric laminates are described in more detail below and with reference to the Figures.

Elastic Film

In some implementations, the elastic film (e.g., film 10) is formed from one or more elastomeric polymers that are melt-processable, i.e., thermoplastic. Any of a variety of thermoplastic elastomeric polymers may generally be used including, for example, elastomeric polyesters, elastomeric polyurethanes, elastomeric polyamides, elastomeric copolymers, elastomeric polyolefins, and so forth. In some implementations involving aperturing the film, elastomeric semi-crystalline polyolefins are used due to their unique combination of mechanical and elastomeric properties. That is, the mechanical properties of such semi-crystalline polyolefins allows for the formation of films that readily aperture during thermal bonding, but yet retain their elasticity.

Semi-crystalline polyolefins have or are capable of exhibiting a substantially regular structure. For example, semi-crystalline polyolefins may be substantially amorphous in their undeformed state, but form crystalline domains upon stretching. The degree of crystallinity of the olefin polymer may be from about 3% to about 30%, in some embodiments from about 5% to about 25%, and in some embodiments, from about 5% and about 15%. Likewise, the semi-crystalline polyolefin may have a latent heat of fusion (ΔHf), which is another indicator of the degree of crystallinity, of from about 15 to about 75 Joules per gram ("J/g"), in some embodiments from about 20 to about 65 J/g, and in some embodiments, from 25 to about 50 J/g. The semi-crystalline polyolefin may also have a Vicat softening temperature of from about 10° C. to about 100° C., in some embodiments from about 20° C. to about 80° C., and in some embodiments, from about 30° C. to about 60° C. The semi-crystalline polyolefin may have a melting temperature of from about 20° C. to about 120° C., in some embodiments from about 35° C. to about 90° C., and in some embodiments, from about 40° C. to about 80° C. The latent heat of fusion (ΔHf) and melting temperature may be determined using differential scanning calorimetry ("DSC") in accordance with ASTM D-3417 as is well known to those skilled in the art. The Vicat softening temperature may be determined in accordance with ASTM D-1525.

Exemplary semi-crystalline polyolefins include polyethylene, polypropylene, blends and copolymers thereof. In one particular embodiment, a polyethylene is employed that is a copolymer of ethylene and an α-olefin, such as a C3-C20 α-olefin or C3-C12 α-olefin. Suitable α-olefins may be linear or branched (e.g., one or more C1-C3 alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

The density of the polyethylene may vary depending on the type of polymer employed, but generally ranges from 0.85 to 0.96 grams per cubic centimeter ("g/cm3"). Polyethylene "plastomers", for instance, may have a density in the range of from 0.85 to 0.91 g/cm3. Likewise, "linear low density polyethylene" ("LLDPE") may have a density in the range of from 0.91 to 0.940 g/cm3; "low density polyethylene" ("LDPE") may have a density in the range of from 0.910 to 0.940 g/cm3; and "high density polyethylene" ("HDPE") may have density in the range of from 0.940 to 0.960 g/cm3. Densities may be measured in accordance with AS™ 1505.

Example polyethylene copolymers include those that are "linear" or "substantially linear." The term "substantially linear" means that, in addition to the short chain branches attributable to comonomer incorporation, the ethylene polymer also contains long chain branches in that the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some implementations, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

Example plastomers for use in forming the film include ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. Still other suitable ethylene polymers are available from The Dow Chemical Company under the designations DOWLEX™ (LLDPE) and ATTANE™ (ULDPE). Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai. et al.; and U.S. Pat. No. 5,278,272 to Lai, et al., which are incorporated herein in their entirety by reference thereto for all purposes.

Other polymers, for example, propylene polymers may also be suitable for use as a semi-crystalline polyolefin. Suitable plastomeric propylene polymers may include, for instance, copolymers or terpolymers of propylene include copolymers of propylene with an α-olefin (e.g., C3-C20), such as ethylene, 1-butene, 2-butene, the various pentene isomers, 1-hexene, 1-octene, 1-nonene, 1-decene, 1-undecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some implementations from about 1 wt. % to about 20 wt. %, and in some embodiments, from about 2 wt. % to about 10 wt. %. Preferably, the density of the polypropylene (e.g., propylene/α-olefin copolymer) may be 0.91 grams per cubic centimeter (g/cm3) or less, in some embodiments, from 0.85 to 0.88 g/cm3, and in some implementations, from 0.85 g/cm3 to 0.87 g/cm3. Suitable propylene polymers are commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 6,500,563 to Datta. et al.; U.S. Pat. No. 5,539,056 to Yang, et al.; and U.S. Pat. No. 5,596,052 to Resconi, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-bu-tylcyclopentadienyl)zirconium dichloride, bis(cyclopentadi-enyl)scandium chloride, bis(indenyl)zirconium dichloride, bis(methylcyclopentadienyl)titanium dichloride, bis(meth-ylcyclopentadienyl)zirconium dichloride, cobaltocene, cyclopentadienyltitanium trichloride, ferrocene, hafnocene dichloride, isopropyl(cyclopentadienyl-1-flourenyl)zirco-nium dichloride, molybdocene dichloride, nickelocene, niobocene dichloride, ruthenocene, titanocene dichloride, zirconocene chloride hydride, zirconocene dichloride, and so forth. Polymers made using metallocene catalysts typi-cally have a narrow molecular weight range. For instance, metallocene-catalyzed polymers may have polydispersity numbers (Mw/Mn) of below 4, controlled short chain branching distribution, and controlled isotacticity.

The melt flow index (MI) of the semi-crystalline poly-olefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when/ subjected to a force of 5000 grams in 10 minutes at 190° C., and may be determined in accordance with AS™ Test Method D1238-E.

Of course, other thermoplastic polymers may also be used to form the elastic film, either alone or in conjunction with the semi-crystalline polyolefins. For instance, a substantially amorphous block copolymer may be employed that has at least two blocks of a monoalkenyl arene polymer separated by at least one block of a saturated conjugated diene polymer. The monoalkenyl arene blocks may include sty-rene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene blocks may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth.

Example thermoplastic elastomeric copolymers are avail-able from Kraton Polymers LLC of Houston, Tex. under the trade name KRATON®. KRATON® polymers include sty-rene-diene block copolymers, such as styrene-butadiene, styrene-isoprene, styrene-butadiene-styrene, and styrene-isoprene-styrene. KRATON® polymers also include sty-rene-olefin block copolymers formed by selective hydroge-nation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These block copolymers may have a linear, radial or star-shaped molecular configuration. Specific KRATON® block copo-lymers include those sold under the brand names G 1652, G 1657, G 1730, MD6673, and MD6973. Various suitable styrenic block copolymers are described in U.S. Pat. Nos. 4,663,220, 4,323,534, 4,834,738, 5,093,422 and 5,304,599, which are hereby incorporated in their entirety by reference thereto for all purposes. Other commercially available block copolymers include the S-EP-S elastomeric copolymers available from Kuraray Company, Ltd. of Okayama, Japan, under the trade designation SEPTON®. Still other suitable copolymers include the S-I-S and S-B-S elastomeric copo-lymers available from Dexco Polymers of Houston, Tex. under the trade designation VECTOR®. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly(ethylene-propylene)-styrene-poly(ethylene-propylene) ("S-EP-S-EP") block copolymer.

The amount of elastomeric polymer(s) employed in the film may vary, but is typically about 30 wt. % or more of the film, in some embodiments about 50 wt. % or more, and in some embodiments, about 80 wt. % or more of the of the film. In one embodiment, for example, the semi-crystalline polyolefin(s) constitute about 70 wt. % or more of the film, in some embodiments about 80 wt. % or more of the film, and in some embodiments, about 90 wt. % or more of the film. In other embodiments, blends of semi-crystalline poly-olefin(s) and elastomeric block copolymer(s) may be employed. In such embodiments, the block copolymer(s) may constitute from about 5 wt. % to about 50 wt. %, in some embodiments from about 10 wt. % to about 40 wt. %, and in some embodiments, from about 15 wt. % to about 35 wt. % of the blend. Likewise, the semi-crystalline polyolefin (s) may constitute from about 50 wt. % to about 95 wt. %, in some embodiments from about 60 wt. % to about 90 wt. %, and in some embodiments, from about 65 wt. % to about 85 wt. % of the blend. It should of course be understood that other elastomeric and/or non-elastomeric polymers may also be employed in the film.

Besides polymers, the elastic film may also contain other components as is known in the art. In one embodiment, for example, the elastic film contains a filler. Fillers are par-ticulates or other forms of material that may be added to the film polymer extrusion blend and that will not chemically interfere with the extruded film, but which may be uniformly dispersed throughout the film. Fillers may serve a variety of purposes, including enhancing film opacity and/or breath-ability (i.e., vapor-permeable and substantially liquid-imper-meable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCor-mack, et al.; U.S. Pat. No. 5,932,497 to Morman, et al.; U.S. Pat. No. 6,461,457 to Taylor, et al., which are incorporated herein in their entirety by reference thereto for all purposes.

The fillers may have a spherical or non-spherical shape with average particle sizes in the range of from about 0.1 to about 7 microns. Examples of suitable fillers include, but are not limited to, calcium carbonate, various kinds of clay, silica, alumina, barium carbonate, sodium carbonate, mag-nesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives. A suitable coating, such as stearic acid, may also be applied to the filler particles if desired. When utilized, the filler content may vary, such as from about 25 wt. % to about 75 wt. %, in some embodiments, from about 30 wt. % to about 70 wt. %, and in some embodiments, from about 40 wt. % to about 60 wt. % of the film.

Other additives may also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals of under the trade name "Irganox®", such as Irganox® 1076, 1010, or E 201. Moreover, bonding agents may also be added to the film to facilitate bonding of the film to additional materials (e.g., nonwoven web). When employed, such additives (e.g., tackifier, antioxidant, stabilizer, etc.) may each be present in an amount from about 0.001 wt. % to about 25 wt. %, in some embodiments, from about 0.005 wt. % to about 20 wt. %, and in some embodiments, from 0.01 wt. % to about 15 wt. % of the film.

The elastic film may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a semi-crystalline polyolefin. In such embodiments, the skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web. For example, the skin layer(s) may be formed from an olefin polymer or blends thereof, such as described above. Additional film-forming polymers that may be suitable for use, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

The thickness of the skin layer(s) is generally selected so as not to substantially impair the elastomeric properties of the film. To this end, each skin layer may separately comprise from about 0.5% to about 15% of the total thickness of the film, and in some embodiments from about 1% to about 10% of the total thickness of the film. For instance, each skin layer may have a thickness of from about 0.1 to about 10 micrometers, in some embodiments from about 0.5 to about 5 micrometers, and in some embodiments, from about 1 to about 2.5 micrometers. Likewise, the base layer may have a thickness of from about 1 to about 40 micrometers, in some embodiments from about 2 to about 25 micrometers, and in some embodiments, from about 5 to about 20 micrometers.

The properties of the resulting film may generally vary as desired. For instance, prior to stretching, the film typically has a basis weight of about 100 grams per square meter or less, and in some embodiments, from about 50 to about 75 grams per square meter. Upon stretching, the film typically has a basis weight of about 60 grams per square meter or less, and in some embodiments, from about 15 to about 35 grams per square meter. The stretched film may also have a total thickness of from about 1 to about 100 micrometers, in some embodiments, from about 10 to about 80 micrometers, and in some embodiments, from about 20 to about 60 micrometers.

Nonwoven Web Material/Facing

As will be described in more detail below, the polymers used to form the nonwoven web material (an example of which is the extensible facing or elastomeric facing) typically have a softening temperature that is higher than the temperature imparted during bonding and are extensible or elastomeric. In this manner, the polymers do not substantially soften during bonding to such an extent that the fibers of the nonwoven web material become completely melt flowable. For instance, polymers may be employed that have a Vicat softening temperature (ASTM D-1525) of from about 100° C. to about 300° C., in some embodiments from about 120° C. to about 250° C., and in some embodiments, from about 130° C. to about 200° C. Exemplary high-softening point polymers for use in forming nonwoven web materials may include, for instance ExxonMobil™ PP3155 (inelastic) and Achieve™ Advanced PP3854 and Dow™ ASPUN 6850.

Extensible or elastomeric monocomponent and/or multi-component fibers may be used to form the nonwoven web material, e.g., facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. and so forth. Various methods for forming multicomponent fibers are described in U.S. Pat. Nos. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference thereto for all purposes.

In some implementations, the polymers of the multicomponent fibers of the extensible or elastomeric facing are spunbond fibers made from thermoplastic materials with different glass transition or melting temperatures where a first component (e.g., sheath) melts at a temperature lower than a second component (e.g., core). Softening or melting of the first polymer component of the multicomponent fiber allows the multicomponent fibers to form a tacky skeletal structure, which upon cooling, stabilizes the fibrous structure. For example, the multicomponent fibers may have from about 20% to about 80%, and in some embodiments, from about 40% to about 60% by weight of the low melting polymer. Further, the multicomponent fibers may have from about 80% to about 20%, and in some embodiments, from about 60% to about 40%, by weight of the high melting polymer. In some implementations, the core of the sheath-core bicomponent fibers include a polypropylene homopolymer or copolymer based on either Ziegler-Natta catalysts or single site catalysts and/or the sheath of the sheath-core bicomponent fibers include homopolymers, copolymers or mixtures thereof from ethylene, propylene, or styrenic derived polymers In some implementations, the nonwoven web (e.g., facing) is a multi-layered spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of, for example, a spunbond web, which have been bonded together to form the nonwoven web. These individually produced layers may differ in terms of production method, basis weight, composition, and fibers as discussed above.

In some implementations, the nonwoven web material may be necked in one or more directions prior to lamination to the film. Suitable techniques necking techniques are described in U.S. Pat. Nos. 5,336,545, 5,226,992, 4,981,747 and 4,965,122 to Morman, as well as U.S. patent application Publication No. 2004/0121687 to Morman, et al. Alternatively, the nonwoven web may remain relatively inextensible in at least one direction prior to lamination to the film. In such embodiments, the nonwoven web may be optionally stretched in one or more directions subsequent to lamination to the film.

The basis weight of the nonwoven web material may generally vary, such as from about 5 grams per square meter ("gsm") to 200 gsm, in some embodiments from about 10 gsm to about 70 gsm, and in some embodiments, from about 15 gsm to about 35 gsm. When multiple nonwoven web materials, such materials may have the same or different basis weights.

As described above, in some implementations the nonwoven web is made from monocomponent spunbond fibers. In other implementations the nonwoven web is made from bicomponent spunbond fibers. In these implementations, for example, the bicomponent fiber contains a polyethylene sheath and a polypropylene based elastomeric core, where the core (but not the sheath) may contain a secondary amide non-blocking additive, which can further improve the garment-like feel of the facing.

For example, in one aspect, the secondary amide additive is erucamide, oleamide, oleyl palmitamide, ethylene bis-oleamide, stearyl erucamide, or combinations thereof. Of course, it should be understood that, in one aspect, the secondary amide may be a non-fatty acid amide.

Regardless of the secondary amide selected, in one aspect, the secondary amide is present in the core in an amount of about 0.1% to about 10% by weight based upon the weight of the core, such as about 0.25% to about 5%, such as about 0.5% to about 2.5%, such as about 0.6% to about 1.5%, such as about 0.7% to about 1%, or any ranges or values therebetween. Particularly, the present disclosure has found that surprisingly, the secondary amide in the core provides improved spinnability and non-blocking properties to the bicomponent fiber, even when used in small amounts in the core Moreover, in one aspect, the sheath(s) is/are formed from one or more ethylene or propylene polymers, such as one or more generally non-elastomeric ethylene or propylene polymers. Thus, in one aspect, the non-elastomeric polyolefin may include generally inelastic polymers, such as conventional polyolefins, (e.g., polyethylene), low density polyethylene (LDPE), Ziegler-Natta catalyzed linear low density polyethylene (LLDPE), etc.), ultra low density polyethylene (ULDPE), polypropylene, polybutylene, etc.; polytetrafluoroethylene; polyesters, e.g., polyethylene terephthalate (PET), etc.; polyvinyl acetate; polyvinyl chloride acetate; polyvinyl butyral; acrylic resins, e.g., polyacrylate, polymethylacrylate, polymethylmethacrylate, etc.; polyamides, e.g., nylon; polyvinyl chloride; polyvinylidene chloride; polystyrene; polyvinyl alcohol; polyurethanes; polylactic acid; copolymers and mixtures thereof; and so forth. For instance, the sheath(s) can include an LLDPE available from Dow Chemical Co. of Midland, Mich., such as DOWLEX™ 2517 or DOWLEX™ 2047, or a combination thereof, or Westlake Chemical Corp. of Houston, Tex. Furthermore, in one aspect, the non-blocking polyolefin material may be other suitable ethylene polymers, such as those available from The Dow Chemical Company under the designations ASPUN™ (LLDPE) and ATTANE™ (ULDPE). available from The Dow Chemical Company under the designations DOWLEX™ (LLDPE), ASPUN™ (LLDPE), and ATTANE™ (ULDPE).

Further, in an aspect, the core is formed from a propylene polymer and/or copolymer. Thus, in one aspect, the core is formed from a propylene-based copolymer plastomers, such as a propylene-based copolymer commercially available under the designations VISTAMAXX™ (e.g., 2330, 6202, and 6102), a propylene-ethylene copolymer-based plastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich.

Regardless of the elastomer(s) and non-elastomeric polyolefin selected, in one aspect the core is present in an amount of about 50% to about 97.5% by weight of the total weight of the elastomeric composition, such as about 60% to about 95%, such as about 70% to about 92.5%, such as about 80% to about 90%, such as about 82.5% to about 87.5% by weight of the total weight of the elastomeric composition, or any ranges or values therebetween.

Figure 1B:
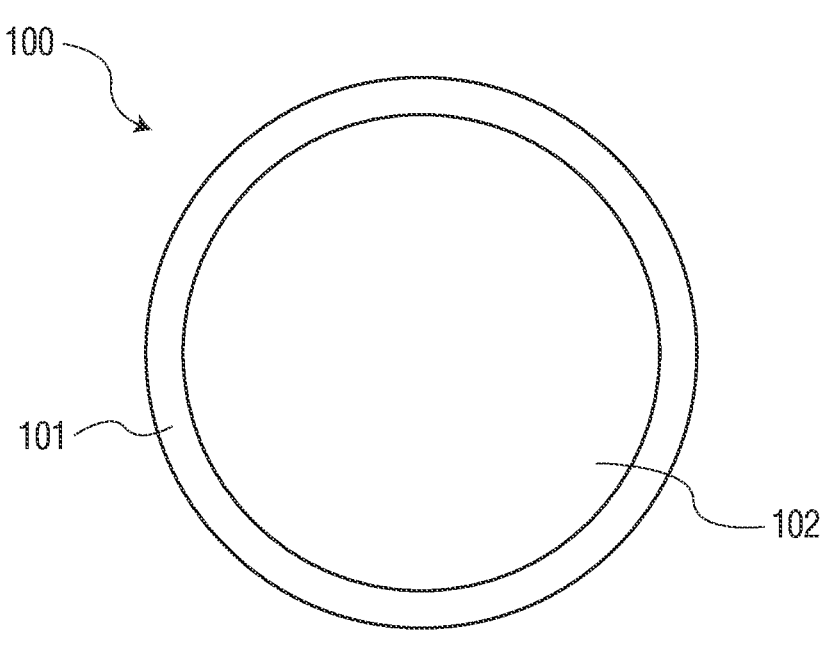

Referring to FIGS. 1A and 1B, respectively, a monocomponent fiber 110 and a bicomponent fiber 100 utilizing a sheath/core arrangement is shown are shown. With respect to bicomponent fiber 100, the core 102 can be formed from a first polymer while the sheath 101 can be formed from a second polymer. Generally, the composition of the monocomponent fiber 110 or the core 102 of the bicomponent fiber can be chosen such that the resulting overall material is elastic, cloth-like, drapable, and soft, and the composition of the sheath 101 of the bicomponent fiber 100 can be chosen such that the sheath 101 provides some blocking properties, while not impacting the garment-like feel of the sheath 101. One such example bicomponent fiber suitable for use herein in the facing/nonwoven material is described in U.S. Patent Application Ser. No. 63/003427, filed on Apr. 1, 2020, entitled, "Elastic Bicomponent Fiber Having Unique Handfeel," the entire contents of which are hereby incorporated by referenced including, without limitation, the composition of the claimed elastomeric bicomponent spunbond fiber and resulting nonwoven formed from that fiber.

Figure 2:
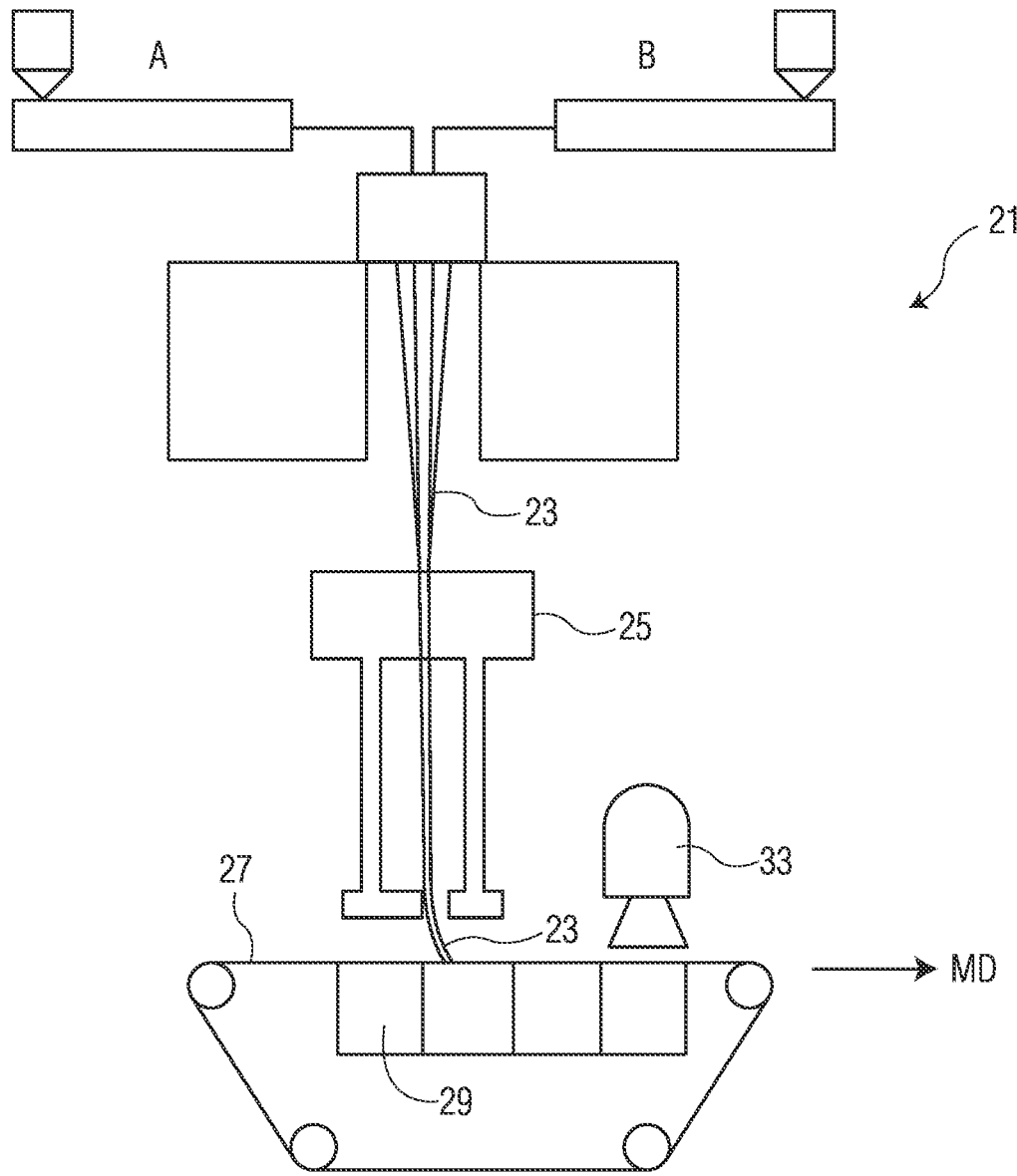
FIG. 2 is an example schematic of an apparatus for forming an extensible facing.
Figure 3:
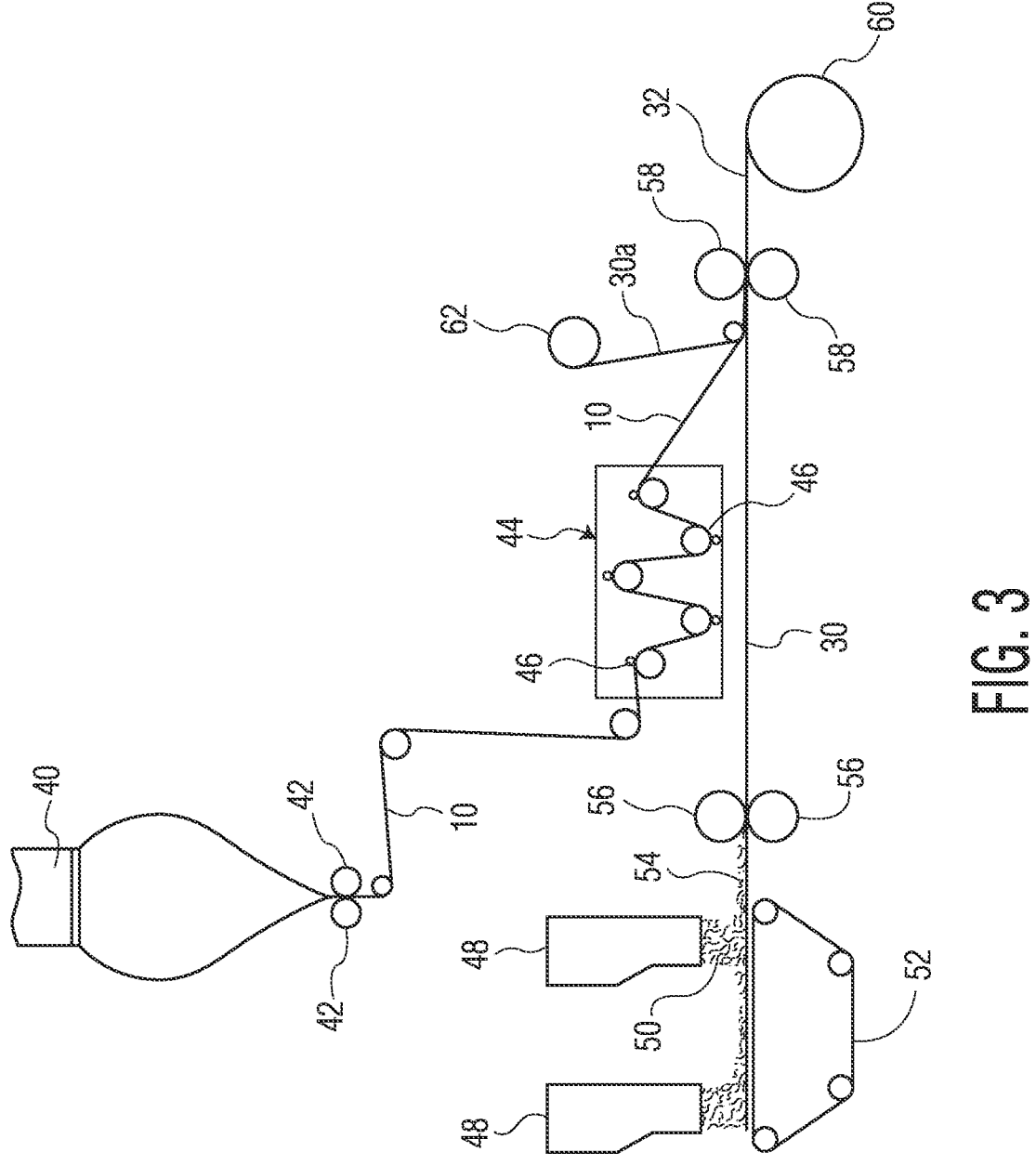
FIG. 3 is an example schematic of an apparatus for forming an elastomeric laminate.

FIG. 2 shows and example process for forming elastomeric, monocomponent or bicomponent spunbond fibers. More specifically, the example process in FIG. 2 is configured to form substantially continuous fibers (e.g., to make an extensible or elastomeric facing 30 as shown in FIG. 3). More particularly, in the case of a bicomponent fiber, different polymer compositions A (e.g., for the sheath) and B (for the core) are initially supplied to a fiber spinning apparatus 21 to form bicomponent fibers 23. Or, in the case of a monocomponent fiber, only one polymer type (e.g., which could include a blended polymer with or without additives) is supplied to a fiber spinning apparatus 21. Once formed, the fibers 23 are traversed through a fiber draw unit 25 and deposited on a moving forming wire 27. Deposition of the fibers is aided by an under-wire vacuum supplied by a suction box 29 that pulls down the fibers 23 onto the forming wire 27. The forming wire 27 is porous so that vertical air flow created by the suction box 29 can cause the fibers to lie down. In one aspect of the present disclosure, the flow rate of this air flow can be kept relatively low to enhance the tendency of the fibers 23 to remain oriented in the MD direction. Alternatively, the suction box 29 can contain sections that extend in the machine direction to disrupt the vertical air flow with at the point where the fibers are laid onto the moving web, thereby allowing the fibers to have a higher degree of orientation in the machine direction. One example of such a technique is described, for instance, in U.S. Pat. No. 6,331,268.

Of course, other techniques may also be employed to help fibers remain oriented in the machine direction. For example, deflector guide plates or other mechanical elements can be employed, such as described in U.S. Pat. Nos. 5,366,793 and 7,172,398. The direction of the air stream used to attenuate the fibers as they are formed can also be used to adjust to effect machine direction orientation, such as described in U.S. Pat. No. 6,524,521. Apart from process described above, other known techniques may also be employed to form the fibers. In one aspect, for example, the fibers may be quenched after they are formed and then directly deposited onto a forming wire without first being drawn in the manner described above. In such aspects, as described above, the flow rate of this air flow can be kept relatively low to enhance the tendency of the fibers to remain oriented in the MD direction, however, it should be understood that, in one aspect, the fibers are not oriented in primarily the MD direction.

Referring again to FIG. 2, once the fibers 23 are formed, they may be heated by a diffuser 33, which can blow hot air onto the surface of the fibers to lightly bond them together for further processing. A hot air knife may also be employed as an alternative to the diffuser. Other techniques for providing integrity to the web may also be employed, such heated calender rolls. In any event, the resulting fibers may then be bonded to form a consolidated, coherent nonwoven web structure, for example, to create the elastomeric facing of the present disclosure. Any suitable bonding technique may generally be employed in the present disclosure, such as adhesive or autogenous bonding (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with polymer composition used to form the fibers. Suitable autogenous bonding techniques may include ultrasonic bonding, thermal bonding, through-air bonding, and so forth. Thermal point bonding, for instance, typically employs a nip formed between two rolls, at least one of which is patterned. Ultrasonic bonding, on the other hand, typically employs a nip formed between a sonic horn and a patterned roll. Although the above describes in detail the use of bicomponent fibers, extensible or elastomeric monocomponent fibers can also be used to create the fibers for the nonwoven web material (e.g., facing).

The spunbond web may also be subjected to one or more additional post-treatment steps. For example, the spunbond web may be stretched in the cross-machine direction using known techniques, such as tenter frame stretching, groove roll stretching, etc. The spunbond web may also be subjected to other known processing steps, such as aperturing, heat treatments, etc.

For example, as indicated above, the spunbond web may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth, and may be uniquely situated for wearable articles due to its improved garment-like feel.

Lamination

In some implementations, laminating the non-woven material to the film involves for example, thermal bonding, adhesive bonding, ultrasonic bonding, pressure bonding, pin aperturing, or some combination thereof.

In some implementations, to concurrently form apertures and bonds between the film and the nonwoven web material, lamination is generally accomplished through a patterned bonding technique (e.g., thermal point bonding, ultrasonic bonding, etc.) in which the materials are supplied to a nip defined by at least one patterned roll. An example of this concurrent aperturing and bonding is described in U.S. Pat. No. 7,803,244 to Siqueira et al., which is incorporated herein in its entirety by reference thereto for all purposes. Thermal point bonding, for instance, typically employs a nip formed between two rolls, at least one of which is patterned. Ultrasonic bonding, on the other hand, typically employs a nip formed between a sonic horn and a patterned roll.

More specifically, the patterned roll, for example, contains a plurality of raised bonding elements to concurrently bond the film to the nonwoven web material(s) and form apertures in the film. The size of the bonding elements may be specifically tailored to facilitate the formation of apertures in the film and enhance bonding between the film and the nonwoven material(s). For example, the bonding elements are typically selected to have a relatively large length dimension. The length dimension of the bonding elements may be from about 300 to about 5000 micrometers, in some embodiments from about 500 to about 4000 micrometers, and in some embodiments, from about 1000 to about 2000 micrometers. The width dimension of the bonding elements may likewise range from about 20 to about 500 micrometers, in some embodiments from about 40 to about 200 micrometers, and in some embodiments, from about 50 to about 150 micrometers. In addition, the "element aspect ratio" (the ratio of the length of an element to its width) may range from about 2 to about 100, in some embodiments from about 4 to about 50, and in some embodiments, from about 5 to about 20.

Besides the size of the bonding elements, the overall bonding pattern may also be selectively controlled to achieve the desired aperture formation. In one embodiment, for example, a bonding pattern is selected in which the longitudinal axis (longest dimension along a center line of the element) of one or more of the bonding elements is skewed relative to the machine direction ("MD") of the elastic film. For example, one or more of the bonding elements may be oriented from about 30° to about 150°, in some embodiments from about 45° to about 135°, and in some embodiments, from about 60° to about 120° relative to the machine direction of the film. In this manner, the bonding elements will present a relatively large surface to the film in a direction substantially perpendicular to that which the film moves. This increases the area over which shear stress is imparted to the film and, in turn, facilitates aperture formation.

The pattern of the bonding elements is generally selected so that the nonwoven composite has a total bond area of less than about 50% (as determined by conventional optical microscopic methods). In some implementations, the film is tensioned and then laminated to the non-woven web with a total bond area of between 5% and 30%.

Figure 4:
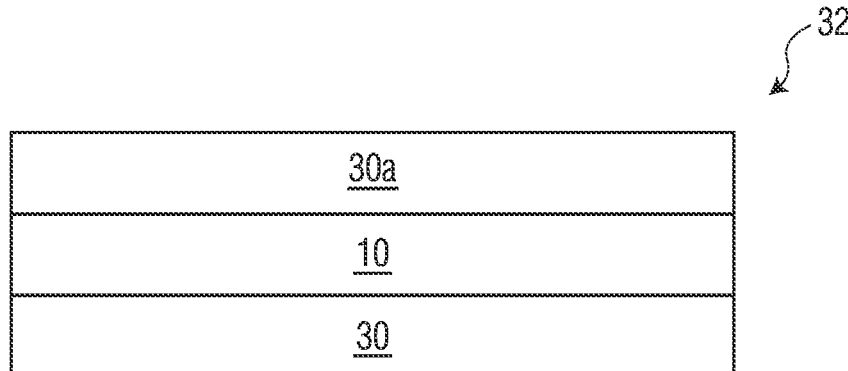
FIG. 4 is an example block representation of an elastomeric laminate.

In some implementations, the bond density is also typically greater than about 50 bonds per square inch, and in some embodiments, from about 75 to about 500 pin bonds per square inch. One suitable bonding pattern for use with this new elastomeric laminate is known as an "S-weave" pattern and is described in U.S. Pat. No. 5,964,742 to McCormack, et al., which is incorporated herein in its entirety by reference thereto for all purposes. S-weave patterns typically have a bonding element density of from about 50 to about 500 bonding elements per square inch, and in some embodiments, from about 75 to about 150 bonding elements per square inch. An example of a suitable "S-weave" pattern in shown in FIG. 2, which illustrates S-shaped bonding elements 88 having a length dimension "L" and a width dimension "W." Another suitable bonding pattern is known as the "rib-knit" pattern and is described in U.S. Pat. No. 5,620,779 to Levy, et al., which is incorporated herein in its entirety by reference thereto for all purposes. Rib-knit patterns typically have a bonding element density of from about 150 to about 400 bonding elements per square inch, and in some embodiments, from about 200 to about 300 bonding elements per square inch. An example of a suitable "rib-knit" pattern in shown in FIG. 3, which illustrates bonding elements 89 and bonding elements 91, which are oriented in a different direction. Yet another suitable pattern is the "wire weave" pattern, which has a bonding element density of from about 200 to about 500 bonding elements per square inch, and in some embodiments, from about 250 to about 350 bonding elements per square inch. An example of a suitable "wire-weave" pattern in shown in FIG. 4, which illustrates bonding elements 93 and bonding elements 95, which are oriented in a different direction. Other bond patterns that may be used are described in U.S. Pat. No. 3,855,046 to Hansen et al.; U.S. Pat. No. 5,962,112 to Haynes et al.; U.S. Pat. No. 6,093,665 to Sayovitz et al.; D375,844 to Edwards, et al.; D428,267 to Romano et al.; and D390,708 to Brown, which are incorporated herein in their entirety by reference thereto for all purposes.

To achieve such concurrent aperture and bond formation without substantially softening the polymer(s) of the nonwoven web material, the bonding temperature and pressure may be selectively controlled. For example, one or more rolls may be heated to a surface temperature of from about 50° C. to about 160° C., in some embodiments from about 60° C. to about 140° C., and in some embodiments, from about 70° C. to about 120° C. Likewise, the pressure exerted by rolls ("nip pressure") during thermal bonding may range from about 75 to about 600 pounds per linear inch, in some embodiments from about 100 to about 400 pounds per linear inch, and in some embodiments, from about 120 to about 200 pounds per linear inch. Of course, the residence time of the materials may influence the particular bonding parameters employed.

As stated, another factor that influences concurrent aperture and bond formation is the degree of tension in the film during lamination. An increase in film tension, for example, typically correlates to an increase in aperture size. Of course, a film tension that is too high may adversely affect the integrity of the film. Thus, in some implementations, a stretch ratio of about 1.5 or more, or 2 to 6 or 2.5 to 7.0, or 3.0 to 5.5, is used to achieve the desired degree of tension in the film during lamination. The stretch ratio may be determined by dividing the final length of the film by its original length. The stretch ratio may also be approximately the same as the draw ratio, which may be determined by dividing the linear speed of the film during lamination (e.g., speed of the nip rolls) by the linear speed at which the film is formed (e.g., speed of casting rolls or blown nip rolls).

The film may be "pre-stretched" (prior to lamination) by rolls rotating at different speeds of rotation so that the sheet is stretched to the desired stretch ratio in the machine direction. For example, the film may be stretched to a ratio of between 2 and 6 in the machine direction, i.e., 2 to 6 times the film's unstretched length. This uniaxially stretched film may also be oriented in the cross-machine direction to form a "biaxially stretched" film. The orientation temperature profile during the "pre-stretching" operation is generally below the melting point of one or more polymers in the film, but high enough to enable the composition to be drawn or stretched. For example, the film may be stretched at a temperature from about 15° C. to about 50° C., in some embodiments from about 25° C. to about 40° C., and in some embodiments, from about 30° C. to about 40° C. When "pre-stretched" in the manner described above, the degree of stretch during lamination may be increased, maintained, or slightly reduced (retracted) to desired degree of tension.

In other implementations, the lamination process does not involve aperturing the film, but rather is directed to bonding the film to the nonwoven web material (e.g., extensible or elastomeric facing). Laminating without intentionally creating apertures can be accomplished through, for example, thermal bonding, adhesive bonding, ultrasonic bonding, and/or pressure bonding.

FIG. 3 shows an example method for forming a composite from an elastic film and a nonwoven web material. The raw materials of the film (e.g., elastomeric polymer) may be dry mixed together (i.e., without a solvent) and added to a hopper (not shown) of an extrusion apparatus 40. The raw materials may alternatively be blended with a solvent. In the hopper, the materials are dispersively mixed in the melt and compounded, such as, batch and/or continuous compounding techniques that employ, for example, a Banbury mixer, Farrel continuous mixer, single screw extruder, twin screw extruder, etc.

The compounded material (not shown) supplied to the extrusion apparatus 40 is then blown into nip rolls 42 to form a single-layered precursor elastic film 10. The rolls 42 may be kept at temperature sufficient to solidify and quench the precursor elastic film 10 as it is formed, such as from about 20 to 60° C. Typically, the resulting precursor elastic film is generally unapertured, although it may of course possess small cuts or tears as a result of processing.

The film 10 is stretched and thinned in the machine direction by passing it through a film-orientation unit or machine direction orienter ("MDO") 44, such as commercially available from Marshall and Willams, Co. of Providence, R.I. In some implementations, the MDO has a plurality of stretching rolls 46 that progressively stretch and thin the film 10 in the machine direction. While four pairs of rolls 46 are illustrated in FIG. 3, it should be understood that the number of rolls may be higher or lower, depending on the level of stretch that is desired and the degrees of stretching between each roll. The film 10 may also be stretched in other directions. For example, the film 10 may be clamped at its lateral edges by chain clips and conveyed into a tenter oven. In the tenter oven, the film 10 may be drawn in the cross-machine direction to the desired stretch ratio by chain clips diverged in their forward travel.

A nonwoven web material 30 is laminated to the elastic film 10. For example, the nonwoven web material 30 may be unwound from a supply roll or made in line, and may be the extensible or elastic facing described above in the "Nonwoven Web Material/Facing" section. FIG. 2, as described above shows one example process for forming a nonwoven web material suitable for use herein. Additionally, FIG. 3 also shows a summary formation process for the nonwoven web material 30. In FIG. 3, the nonwoven web material 30 may be formed, for example, by spunbond extruders 48. The extruders 48 deposit fibers 50 (e.g., bicomponent fibers) onto a forming wire 52, which is part of a continuous belt arrangement that circulates around a series of rolls. If desired, a vacuum (not shown) may be utilized to maintain the fibers on the forming wire 52. The spunbond fibers 50 form a web 54 (e.g., the spunbond web 23 of FIG. 2) that may optionally be compressed via compaction rolls 56. Although not necessarily required, a second material 30a originating from a supply roll 62 may also be laminated to the elastic film 10. The second material 30 a may be a second nonwoven web material, film, etc. Further, additional layers or nonwoven web material and/or films may be laminated to the film 10 and nonwoven web 30.

Although other processes can be used such as adhesive bonding, ultrasonic bonding, pressure bonding, and/or pin aperturing, in some implementations, thermal bonding techniques are used to laminate the nonwoven web material(s) to the elastic film 10. In FIG. 3, for example, the materials 30 and 30a are directed to a nip defined between rolls 58 for laminating to the elastic film 10. One or both of the rolls 58 may contain a plurality of raised bonding elements and/or may be heated. Upon lamination, the elastic film 10 is melt fused to the nonwoven web materials 30 and 30 a at a plurality of discrete bond sites 31. That is, the elastomeric polymer(s) of the film 10 are softened and/or melted so that they may physically entrap fibers of the nonwoven web materials 30 and 30a. The elastic film 10 may possess a certain tack so that it also adheres to the fibers upon lamination. The resulting laminate 32 is shown, for example, in FIG. 4, which is a block representation of an elastomeric laminate.

The resulting laminate 32 may then be wound and stored on a take-up roll 60. Optionally, the laminate 32 is kept under tension, such as by using the same linear velocity for the roll 60 as the speed of one or more of the stretching rolls 46. However, the composite 32 may be allowed to slightly retract prior to winding on to the take-up roll 60. This may be achieved by using a slower linear velocity for the roll 60.

Because, in some implementations, the elastic film 10 is tensioned prior to lamination, it will, after the tensioned is removed, retract toward its original machine direction length and become shorter in the machine direction, thereby buckling or forming gathers in the laminate 32. The resulting elastic laminate 32 thus becomes extensible in the machine direction to the extent that the gathers or buckles in the laminate 32 may be pulled back out flat and then stretched further by virtue of the extensible nature of the nonwoven web 30, as described above, thereby allowing the elastic film 10 to elongate and even stretch beyond its tensioned length in the machine direction. Further, this extensible laminate 32 (e.g., the nonwoven web 30 bonded to the film 10) can be extensible or elastomeric in the cross-machine direction as the extensible nonwoven web 30 (and the film 10) permit such bi-axial stretching (i.e., stretching in the machine and cross-machine directions).

In some implementations, the laminate 32 may be mechanically stretched in the cross-machine and/or machine directions to enhance extensibility. In one implementation, the laminate 32 may be coursed through two or more rolls that have grooves in the CD and/or MD directions. Such grooved satellite/anvil roll arrangements are described in U.S. patent application Publication Nos. 2004/0110442 to Rhim, et al. and 2006/0151914 to Gerndt, et al., which are incorporated herein in their entirety by reference thereto for all purposes. For instance, the laminate 32 may be coursed through two or more rolls that have grooves in the CD and/or MD directions. The grooved rolls may be constructed of steel or other hard material (such as a hard rubber).

Besides the above-described grooved rolls, other techniques may also be used to mechanically stretch the laminate 32 in one or more directions. For example, the laminate 32 may be passed through a tenter frame that stretches the laminate 32. Such tenter frames are well known in the art and described, for instance, in U.S. patent application Publication No. 2004/0121687 to Morman, et al. The laminate 32 may also be necked. Suitable techniques necking techniques are described in U.S. Pat. Nos. 5,336,545, 5,226,992, 4,981,747 and 4,965,122 to Morman, as well as U.S. patent application Publication No. 2004/0121687 to Morman, et al., all of which are incorporated herein in their entirety by reference thereto for all purposes.

The laminate 32 described above may be used in a wide variety of applications. As noted above, for example, the laminate 32 may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Absorbent articles may include a substantially liquid-impermeable layer (e.g., outer cover), a liquid-permeable layer (e.g., bodyside liner, surge layer, etc.), and an absorbent core.

As noted above, the laminate 32 described above can have improved bi-axial stretch and/or bending length characteristics by virtue of the elastomeric film 10 and the extensible (or elastomeric) nonwoven web material 30 and the lamination process. The effect of these improvements can be seen with respect to the hysteresis values and Cantilever Bend Test performance of the Examples below:

Inventive Example 1 is a 126 gsm laminate with a facing-film-facing construction, where each 17 gsm facing is made from bicomponent polymeric fibers having a composition of 76% propylene/ethylene block copolymer, 20% linear low density polyethylene with the remainder in additives, and the film is made from an elastomer having a 94% olefinic block copolymer elastomer, 5% polypropylene elastomer and 1% additives composition. The laminate is formed by the process described with reference to FIG. 3.

Inventive Example 2 is a 126 gsm laminate with a facing-film-facing construction, where each 17 gsm facing is made from bicomponent polymeric fibers having a composition of a 76% propylene/ethylene block copolymer and isotactic polypropylene blend, 20% linear low density polyethylene and the remainder in additives, and the film is made from an elastomer having a 94% olefinic block copolymer elastomer, 5% polypropylene elastomer and 1% additives composition. The laminate is formed by the process described with reference to FIG. 3.

Inventive Example 3 is a 126 gsm laminate with a facing-film-facing construction, where each 17 gsm facing is made from bicomponent polymeric fibers having a composition of 93% propylene/ethylene block copolymer and isotactic polypropylene blend with the remainder in additives, and the film is made from an elastomer having a 94% olefinic block copolymer elastomer, 5% polypropylene elastomer and 1% additives composition. The laminate is formed by the process described with reference to FIG. 3.

Comparative Example 4 is a 87 gsm laminate with a facing-film-facing construction, where 17 gsm facing is made from monocomponent polymeric fibers having a composition of 100% polypropylene (Exxon 3155), and the film is made from an elastomer having a 94% olefinic block copolymer elastomer, 5% polypropylene elastomer and 1% additives composition. The laminate is formed by the process described with reference to FIG. 3.

More specifically, the hysteresis test (also referred to a cycling test) refers to a method for determining the elastic properties of an extensible material. Further details regarding this test are disclosed in the section entitled "Test for Determining Hysteresis, Set and Elongation/Retraction Ratio" of U.S. Pat. No. 7,320,948. The term "hysteresis" or "hysteresis value" refers to an elastic property of a material determined using the cycling test. Hysteresis is expressed as the percentage of energy recovered upon retraction of an elongated material.

In Table 1, the "Hysteresis Loss—Cycle 1" value for CD is calculated by subtracting the energy recovered during the first cycle retraction from the energy delivered to extend the material in the first cycle extension at forty percent (40%) elongation (i.e., stretching the sample to 1.4 times is unstretched length), this quantity divided by the energy delivered to extend the material in the first cycle extension, this quantity times 100. The energy delivered and the energy recovered were determined by the computer and measured as the area under the stress strain curve.

In Table 2, the "Hysteresis Loss—Cycle 1" value for MD is calculated by subtracting the energy recovered during the first cycle retraction from the energy delivered to extend the material in the first cycle extension at one hundred percent (100%) elongation (i.e., stretching the sample to 2 times is unstretched length), this quantity divided by the energy delivered to extend the material in the first cycle extension, this quantity times 100. The energy delivered and the energy recovered were determined by the computer and measured as the area under the stress strain curve.

The "Percent Set (10 grams) %—Cycle 1" is the value determined by measuring the extension that the sample is at during the retraction cycle when the force first measures 10 grams or lower. The percent set is defined as the maximum extension length the sample is taken to minus the length determined in the 10-gram retraction measurement above, this quantity divided by the maximum extension length, this quantity times 100.

The values in Table 1 below are from the cross-machine direction and averaged from five (5) runs.

TABLE 1

| Example | Hysteresis Loss (%)-Cycle 1 | Percent Set (10 grams) %-Cycle 1 |
|---|---|---|
| 1 | 66.71 | 14.8 |
| 2 | 67.84 | 13.8 |
| 3 | 67.59 | 14.1 |
| 4 | 73.22 | 15.7 |

The values in Table 2 below are from the machine direction, and averaged from five (5) runs.

TABLE 2

| Example | Hysteresis Loss (%)-Cycle 1 | Percent Set (10 grams) %-Cycle 1 |
|---|---|---|
| 1 | 32.27 | 6.98 |
| 2 | 32.63 | 7.04 |
| 3 | 41.25 | 7.9 |
| 4 | 55.1 | 20.4 |

As shown in Table 1, Examples 1, 2 and 3 all have a Hysteresis Loss in the cross-machine direction of less than 72%, less than 70%, between 60% and 72%, between 66% and 70%, between 66% and 68%. The lower the hysteresis loss the better as it suggests the material retains more of its extension and retraction abilities.

As shown in Table 2, Examples 1, 2 and 3 all have a Hysteresis Loss in the machine direction of less than 55%, less than 50%, between 25% and 55%, between 32% and 50% and between 32% and 41%. The lower the hysteresis loss the better as it suggests the material retains more of its extension and retraction abilities.

Given the nonwoven material (e.g., 30) is laid down and oriented in the machine direction, it follows here that the hysteresis loss in the machine direction will be and is better than in the cross-machine direction. However, given the elastomeric nature of the nonwoven web material used herein the laminate composite (e.g., 32) also shows an improved hysteresis loss in the cross-machine direction (see Examples 1, 2 and 3) as compared with the comparative material (see Example 4).

All four Examples were also tested using the Cantilever Bend Test (see ASTM D747-10). The test was performed on a FRL Cantilever Bending Tester made from Testing Machines, Inc., Amityville, N.Y. This involved calibrating the Tester by leveling the Tester to ensure it was level front-to-back and side-to-side so it was not tilted, using a protractor to ensure the measuring arm was set to 42 degrees from horizontal per STS standards, cutting test strips of the Examples in 1×8 inch sections in the forty-five degree (45 degree) machine direction/cross-machine direction (45 MDCD, which is taken at a 45 degree angle from the machine direction), the cross-machine direction and the machine direction, and then feeding out the strip of the Example along it's long axis (i.e., the eight inch axis) until the strip touched the measuring arm, and recording the length of the strip required to be fed out before the strip touched the measuring arm. Each Example was tested five times with a first side up and then five times with the first side down. The averages for each Example for all ten tests in a given direction are shown in Table 3 below.

TABLE 3

| Example | 45 MDCD (centimeters) | CD (cm) | Machine Direction (cm) |
|---|---|---|---|
| 1 | 1.435 | 1.995 | 1.19 |
| 2 | 1.35 | 1.855 | 1.255 |
| 3 | 1.68 | 2.68 | 1.46 |
| 4 | 2.05 | 2.875 | 2.054 |

The values in Table 3 show that Examples 1, 2 and 3 have better results than Example 4, where the lower the 45 MDCD (Cantilever Bend Test) value is the more drapeable the material is, which is often a desirable characteristic for absorbent articles. Drapeability describes the materials ability to relax and form to any surface over which it is laid. Thus increased drapeability characteristically means a more comfortable and clothlike feel, for example, in the garment field. Here the 45 MDCD values for Examples 1,2, 3 are less than 2.05 cm, between 1.3 cm and 2.05 cm, between, between 1.35 cm and 2 cm and between 1.35 cm and 1.68 cm.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

This written description does not limit the invention to the precise terms set forth. Thus, while the invention has been described in detail with reference to the examples set forth above, those of ordinary skill in the art may affect alterations, modifications and variations to the examples without departing from the scope of the invention.

What is claimed:

1. A method comprising:
forming an elastic film from a polymer composition;

tensioning the elastic film to a stretch ratio of between 2 and 6 in the MD;
laminating the elastic film to an extensible facing, to provide an elastomeric laminate having a CD hysteresis loss of 70% or less and an MD hysteresis loss of 50% or less, and/or a 45 MDCD of less than 2.05 cm.

2. The method of claim 1, wherein the tensioned elastic film is laminated to the extensible facing through a process providing between 5 and 30% bond area.

3. The method of claim 1, wherein the polymer composition comprises polyethylene, polypropylene, blends and copolymers thereof.

4. The method of claim 1, wherein the tensioning occurs prior to the laminating.

5. The method of claim 1, wherein the extensible facing comprises monocomponent fibers.

6. The method of claim 1, wherein the extensible facing comprises bicomponent fibers.

7. The method of claim 6, wherein the bicomponent fibers are a sheath/core configuration, wherein the sheath contains a non-elastomeric polymer, and the core contains a polypropylene based elastomer and a secondary amide.

8. The method of claim 1, wherein the CD hysteresis loss is between 60% and 70% and the MD hysteresis loss is between 25% and 50%.

9. The method of claim 1, wherein the laminating comprises one or more of thermal bonding, adhesive bonding, ultrasonic bonding, pressure bonding, and pin aperturing.

10. The method of claim 1, wherein the CD hysteresis loss is between 66% and 70% and the MD hysteresis loss is between 32% and 50%.

11. The method of claim 10 wherein the MD hysteresis loss is between 32% and 40%.

12. The method of claim 1, wherein the elastomeric laminate has a 45 MDCD of between 1.3 cm and 2.05 cm.

13. The method of claim 12, wherein the elastomeric laminate has a 45 MDCD of between 1.35 cm and 2 cm.

14. The method of claim 13, wherein the elastomeric laminate has a 45 MDCD of between 1.35 cm and 1.68 cm.

15. An elastomeric laminate comprising:
an elastic film;
an extensible facing laminated to the elastic film; and
wherein the elastomeric laminate has a CD hysteresis loss of 70% or less and an MD hysteresis loss of 50% or less, and/or wherein the elastomeric laminate has a 45 MDCD of less than 2.05 cm.

16. The elastomeric laminate of claim 15, wherein the CD hysteresis loss is between 70% and 60% and the MD hysteresis loss is between 50% and 25%.

17. The elastomeric laminate of claim 16, wherein the CD hysteresis loss is between 66% and 70% and the MD hysteresis loss is between 32% and 50%.

18. The elastomeric laminate of claim 17, wherein the MD hysteresis loss is between 32% and 40%.

19. The elastomeric laminate of claim 15, wherein the elastomeric laminate has a 45 MDCD of between 1.3 cm and 2.05 cm.

20. The elastomeric laminate of claim 19, wherein the elastomeric laminate has a 45 MDCD of between 1.35 cm and 2 cm.

21. The elastomeric laminate of claim 20, wherein the elastomeric laminate has a 45 MDCD of between 1.35 cm and 1.68 cm.

* * * * *